United States Patent
Meade et al.

(10) Patent No.: US 6,528,699 B1
(45) Date of Patent: *Mar. 4, 2003

(54) TRANSGENICALLY PRODUCED NON-SECRETED PROTEINS

(75) Inventors: Harry Meade, Newton, MA (US); Li-How Chen, Acton, MA (US); Paul DiTullio, Northboro, MA (US)

(73) Assignee: Genzyme Transgenics Corporation, Framingham, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/028,551

(22) Filed: Feb. 24, 1998

Related U.S. Application Data (60) Provisional application No. 60/038,998, filed on Feb. 25, 1997.

(51) Int. Cl.⁷ .......................... C12P 21/00; C12P 21/06; A01K 67/00; C07H 21/02; C07H 21/04
(52) U.S. Cl. ............................ 800/7; 800/14; 435/69.1; 536/23.1; 536/23.5
(58) Field of Search ............................ 800/3, 7, 14, 21, 800/13, 24, 18, 22, 25; 435/320.1, 455, 463, 325, 69.1; 514/44; 536/23.1, 23.5

(56) References Cited

U.S. PATENT DOCUMENTS

| | | | |
|---|---|---|---|
| 4,873,316 A | 10/1989 | Meade et al. | 530/412 |
| 5,304,489 A | 4/1994 | Rosen | 435/320.1 |
| 5,849,992 A | * 12/1998 | Meade et al. | 800/7 |

FOREIGN PATENT DOCUMENTS

| WO | WO92/05446 | 4/1992 | G01N/33/573 |
|---|---|---|---|

OTHER PUBLICATIONS

Niemann et. al.; Transgenic livestock: premises and promises, 2000, Animal Reproduction Science 60–61: 277–293.*
Houdebine; The production of pharmaceutical proteins from the mild of transgenic animals, 1995, Reprod Nutr Dev.35: 609–617.*
Clark; The Mammary Gland as a Bioreactor: Expression, Processing, and Production of Recombinant Proteins, 1998, Journal of Mammary Gland Biology and Neoplasia vol. 3, No. 3: 337–350.*
DiTullio et. al.; Production of Cystic Fibrosis Transmembrane Conductance Regulator in the Milk of Transgenic Mice, 1992, Bio/Technology vol. 10: 74–77.*
Roberts et. al.; Cloning of the goat B–casein–encoding gene and expression in transgenic mice, 1992, Gene 121: 255–262.*
Kawasaki et. al.; Cloning and Expression of Large Isoform of Glutamuc Acid Decarboxylase from Human Pancreatic Islet, 1993, Biochemical and Biophysical Research Communications vol. 192. No. 3: 1353–1359.*
Wilkins et al. Journal of Cellular Biochemistry. 49(4): 333–8, Aug. 1992.*
Bio– Critical Synergy: The Biotechnology Industry and Intellectual Property Protection. Hearing of the US PTO, San Diego, CA, Oct. 1994.*
Lunn et al. Journal of Biological Chemistry. 262(17): 8318–8324, 1987.*
Kelly et al. Annals of Human Genetics. 56(3): 255–265, Jul. 1992.*
Kaufman et al. Nature. 366: 69–72, Nov. 1993.*
Haas et al., "Expression of the myelin basic protein gene in transgenic mice expressing human neurotropic virus, JCV, early protein" Immunology 202:89–96 (1994).
Warren et al., "Administration of myelin basic protein synthetic peptides to multiple sclerosis patients" J. Neurological Sciences 133:85–94 (1995).

* cited by examiner

Primary Examiner—Deborah Crouch
Assistant Examiner—Thaian Ton
(74) Attorney, Agent, or Firm—Fish & Richardson P.C.

(57) ABSTRACT

The invention provides a method of making and secreting a non-secreted protein. The method includes expressing the protein from a nucleic acid construct which includes: (a) a mammary epithelial specific promoter; (b) a milk protein specific signal sequence which can direct the secretion of a protein; (c) optionally, a sequence which encodes a sufficient portion of the amino terminal coding region of a secreted protein to allow secretion in the milk of a transgenic mammal, of the non-secreted protein; and (d) a sequence which encodes a non-secreted protein, wherein elements (a), (b), optionally (c), and (d) are preferably operatively linked in the order recited. Both glutamic acid decarboxylase (GAD) and myelin basic protein (MBP), which are cytoplasmic proteins, have been produced by the methods of the present invention. The invention also provides methods for treating diabetes and multiple sclerosis using proteins produced by the methods of the present invention.

36 Claims, 4 Drawing Sheets

TRANSGENICALLY PRODUCED NON-SECRETED PROTEINS

This application claims the benefit of a previously filed Provisional Application No. 60/038,998, filed Feb. 25, 1997, which is hereby incorporated by reference.

FIELD OF THE INVENTION

This invention relates to the production and secretion of proteins which are not ordinarily secreted.

BACKGROUND OF THE INVENTION

A growing number of recombinant proteins are being developed for therapeutic and diagnostic applications. However, many of these proteins may be difficult or expensive to produce in a functional form and/or in the required quantities using conventional methods. Conventional methods involve inserting the gene responsible for the production of a particular protein into host cells such as bacteria, yeast, or mammalian cells, e.g., COS cells, and then growing the cells in culture media. The cultured cells then synthesize the desired protein. Traditional bacteria or yeast systems may be unable to produce many complex proteins in a functional form. While mammalian cells can reproduce complex proteins, they are generally difficult and expensive to grow, and often produce only mg/L quantities of protein. In addition, non-secreted proteins are relatively difficult to purify from procaryotic or mammalian cells as they are not secreted into the culture medium.

SUMMARY OF THE INVENTION

In general, the invention features, a method of making and secreting a protein which is not normally secreted (a non-secreted protein). The method includes expressing the protein from a nucleic acid construct which includes:

(a) a promoter, e.g., a mammary epithelial specific promoter, e.g., a milk protein promoter;

(b) a signal sequence which can direct the secretion of a protein, e.g. a signal sequence from a milk specific protein;

(c) optionally, a sequence which encodes a sufficient portion of the amino terminal coding region of a secreted protein, e.g., a protein secreted into milk, to allow secretion, e.g., in the milk of a transgenic mammal, of the non-secreted protein; and (d) a sequence which encodes a non-secreted protein, wherein elements (a), (b), optionally (c), and (d) are preferably operatively linked in the order recited.

In preferred embodiments: elements a, b, c (if present), and d are from the same gene; the elements a, b, c (if present), and d are from two or more genes.

In preferred embodiments the secretion is into the milk of a transgenic mammal.

In preferred embodiments: the signal sequence is the β-casein signal sequence; the promoter is the β-casein promoter sequence.

In preferred embodiments the non-secreted protein-coding sequence: is of human origin; codes for a truncated, nuclear, or a cytoplasmic polypeptide; codes for glutamic acid decarboxylase or myelin basic protein.

In preferred embodiments, the protein is a mutant protein which lacks a biological activity of the wild type protein.

In another aspect, the invention features, a nucleic acid construct, preferably an isolated nucleic acid construct, which includes:

(a) a promoter, e.g., a mammary epithelial specific promoter, e.g., a milk protein promoter;

(b) a signal sequence which can direct the secretion of a protein, e.g., a signal sequence from a milk specific protein;

(c) optionally, a sequence which encodes a sufficient portion of the amino terminal coding region of a secreted protein, e.g., a protein secreted into milk, to allow secretion, e.g., in the milk of a transgenic mammal, of the non-secreted protein; and (d) a sequence which encodes a non-secreted protein, wherein elements (a), (b), optionally (c), and (d) are preferably coupled in the order recited.

In preferred embodiments: elements a, b, c (if present), and d are from the same gene; the elements a, b, c (if present), and d are from two or more genes.

In preferred embodiments the secretion is into the milk of a transgenic mammal.

In preferred embodiments: the signal sequence is the β-casein signal sequence; the promoter is the β-casein promoter sequence.

In preferred embodiments the non-secreted protein-coding sequence: is of human origin; codes for a truncated, nuclear, or a cytoplasmic polypeptide; codes for glutamic acid decarboxylase or myelin basic protein.

In preferred embodiments, the protein is inactive, e.g., it is a mutant protein which lacks a biological activity of the wild type protein.

In another aspect, the invention features, a method for providing a non-secreted protein, e.g., a heterologous non-secreted polypeptide, in the milk, of a transgenic mammal. The method includes obtaining milk from a transgenic mammal having introduced into its germline a nucleic acid construct described herein, e.g., a heterologous non-secreted protein-coding sequence operatively linked to a signal and a promoter sequence that result in the preferential expression of the protein-coding sequence in mammary gland epithelial cells, thereby secreting the heterologous non-secreted polypeptide in the milk of the mammal.

In preferred embodiments, the protein is inactive, e.g., it is a mutant protein which lacks a biological activity of the wild type protein.

In preferred embodiments the transgenic mammal is selected from the group consisting of sheep, mice, pigs, cows and goats. The preferred transgenic mammal is a goat.

In preferred embodiments, the promoter is selected from the group consisting of the beta lactoglobulin promoter, whey acid protein promoter, β-casein promoter and the lactalbumin promoter. The preferred promoter is the β-casein promoter.

In preferred embodiments, the signal sequence is β-casein signal sequence.

In preferred embodiments, the non-secreted protein-coding sequence: is of human origin; codes for a truncated, nuclear, or a cytoplasmic polypeptide; codes for glutamic acid decarboxylase or myelin basic protein; codes for an inactive form of glutamic acid decarboxylase.

In preferred embodiments, the protein is fused to other sequences, e.g., to one or both of: a signal sequence, e.g., the signal sequence of β-casein and/or a sequence which encodes a sufficient portion of the amino terminal coding region of a secreted protein, e.g., a protein secreted into milk, to allow secretion, e.g., in the milk of a transgenic mammal, of the non-secreted protein.

In other preferred embodiments the non-secreted polypeptide is purified from the milk of a transgenic mammal.

In another aspect, the invention features, a method of inducing tolerance in a subject to an antigen. The antigen can be a xenoantigen, an alloantigen or a autoantigen. The antigen can be a protein, e.g., a non-secreted protein.

The method includes:
providing a tolerogen expressed in a transgenic mammal which includes the antigen;
and administering the tolerogen to the subject in an amount sufficient to induce tolerance to said protein antigen.

In preferred embodiments: the tolerogen is administered, preferably orally, to the subject in the milk of a transgenic mammal, e.g., a transgenic dairy mammal, e.g., a goat, sheep, or cow. Other mammals, e.g., pigs, can also be used.

In preferred embodiments, the tolerogen is or includes: a protein, e.g., an inactive protein; a non-secreted protein; a fusion of a non-secreted protein and another peptide sequence, e.g., a protein antigen fused to all or part of a secreted protein.

Preferably, the transgenically produced product, is in inactive form, e.g., it is a mutant which lacks an activity of the wild type protein.

In preferred embodiments, the autoantigen is fused to other sequences, e.g., to one or both of: a signal sequence, e.g., the signal sequence of β-casein and/or a sequence which encodes a sufficient portion of the amino terminal coding region of a secreted protein, e.g. a protein secreted into milk, to allow secretion, e.g., in the milk of a transgenic mammal, of the non-secreted protein.

In preferred embodiments, the antigen is: an antigen which is characteristic of an autoimmune disorder, e.g., diabetes, lupus, multiple sclerosis, rheumatoid arthritis; GAD; MBP; a transcription factor.

In preferred embodiments the subject is at risk of developing, or has, an autoimmune disorder, e.g., diabetes, lupus, multiple sclerosis, of rheumatoid arthritis.

In yet another aspect, the invention features, a method of treating insulin-dependent diabetes mellittis (IDDM) in a subject. The method includes administering to the subject therapeutically effective amount of a transgenically produced tolerogen which includes an autoantigen, e.g., glutamic acid decarboxylase, or an effective amount of a fusion protein which includes an autoantigen, e.g., glutamic acid decarboxylase.

In preferred embodiments, the subject is orally administered milk from a transgenic mammal which expresses the transgenically produced tolerogen which includes an autoantigen, e.g., glutamic acid decarboxylase, or an effective amount of a fusion protein which includes an autoantigen, e.g., glutamic acid decarboxylase. Preferably, the transgenically produced tolerogen, e.g., glutamic acid decarboxylase is in inactive form, e.g., it is a mutant which lacks an activity of the wild type protein.

In preferred embodiments, the autoantigen is fused to other sequences, e.g., to one or both of: a signal sequence, e.g., the signal sequence of β-casein and/or a sequence which encodes a sufficient portion of the amino terminal coding region of a secreted protein, e.g., a protein secreted into milk, to allow secretion, e.g., in the milk of a transgenic mammal, of the non-secreted protein.

In still another aspect, the invention features treating multiple sclerosis in a subject. The method includes administering to the subject therapeutically effective amount of a transgenically produced tolerogen which includes an autoantigen, e.g., myelin basic protein, or an effective amount of a fusion protein which includes an autoantigen, e.g., myelin basic protein (MBP).

In preferred embodiments, the subject is orally administered milk from a transgenic mammal which expresses the transgenically produced myelin basic protein, or an effective amount of a fusion protein which includes an autoantigen, e.g., myelin basic protein. Preferably, the transgenically produced tolerogen, e.g., MBP is in inactive form, e.g., it is a mutant which lacks an activity of the wild type protein.

In preferred embodiments, the autoantigen is fused to other sequences, e.g., to one or both of: a signal sequence, e.g., the signal sequence of β-casein and/or a sequence which encodes a sufficient portion of the amino terminal coding region of a secreted protein, e.g. a protein secreted into milk, to allow secretion, e.g., in the milk of a transgenic mammal, of the non-secreted protein.

In another aspect, the invention features, a therapeutic composition which includes a therapeutically effective amount of the transgenieally produced glutamic acid decarboxylase and a pharmaceutically-acceptable carrier or diluent, e.g., the milk of a transgenic mammal. Preferably, the transgenically produced glutamic acid decarboxylase is in inactive form.

In another aspect, the invention features, a therapeutic composition which includes a therapeutically effective amount of the transgenically produced myelin basic protein and a pharmaceutically-acceptable carrier or diluent, e.g., the milk of a transgenic mammal.

In another aspect, the invention features, a fusion protein which includes:
a non-secreted protein, e.g., an inactive non-secreted protein,
a signal sequence which directs the secretion of the protein, e.g., a signal from a secreted protein; and
(optionally) a sequence which encodes a sufficient portion of the amino terminal coding region of a secreted protein, e.g., a protein secreted into milk, to allow secretion, e.g., in the milk of a transgenic mammal, of the non-secreted protein.

In preferred embodiments, the fusion protein includes: the signal sequence and sufficient residues from the amino terminal end of a secreted protein, to allow secretion of the fusion protein in milk, fused to a non-secreted protein. Preferred embodiments include the signal sequence and sufficient residues from the amino terminal end of beta casein, e.g., goat beta casein, fused to a non secreted protein.

In another aspect, the invention features, a composition which includes a tolerogen or other trangenic protein described herein and milk. In preferred embodiments, the milk is the milk of a transgenic mammal which secretes the tolerogen or other protein.

In another aspect, the invention features, a method of inducing tolerance in a transgenic mammal to an antigen. The antigen can be a xenoantigen, an alloantigen or a autoantigen. The antigen can be a protein, e.g., a non-secreted protein, e.g., an inactive protein.

The method includes:
expressing a tolerogen in the milk of the transgenic mammal at a level sufficient to induce tolerance.

In preferred embodiments: the transgenic mammal is a transgenic dairy mammal, e.g., a goat, sheep, or cow. Other mammals, e.g., pigs, can also be used.

In preferred embodiments the tolerogen is or includes: a protein; a protein described herein; a non-secreted protein; a fusion of a non-secreted protein and another peptide sequence, e.g., a protein antigen fused to all or part of a secreted protein.

In preferred embodiments the antigen is: an antigen which is characteristic of an autoimmune disorder, e.g., diabetes, lupus, multiple sclerosis, rheumatoid arthritis; GAD; MBP; a transcription factor.

In another aspect, the invention features, a preparation of milk from a transgenic mammal, which milk includes a protein, e.g., a protein described herein, not normally secreted into the milk of mammals of the species of the transgenic mammal. The transgenic mammal can be a transgenic dairy mammal, e.g., a goat, sheep, or cow. Other mammals, e.g., pigs, can also be used.

In another aspect, the invention features, a transgenically produced non-secreted polypeptide, wherein the polypeptide is secreted.

In preferred embodiments, the transgenically produced non-secreted polypeptide is secreted into the milk of a transgenic mammal.

In preferred embodiments, the transgenically produced non-secreted polypeptide is selected from the group consisting of truncated, nuclear, and cytoplasmic polypeptides. Examples of cytoplasmic polypeptides include, but are not limited to, glutamic acid decarboxylase and myelin basic protein. Preferably, the protein, e.g., glutamic acid decarboxylase, is expressed in an inactive form.

In other preferred embodiments, the transgenic mammal is selected from the group consisting of sheep, mice, pigs, cows and goats. The preferred transgenic mammal is a goat.

In methods herein which induce tolerance by the use of a tolerogen which include a non-secreted protein fragments of the non-secreted protein can be used. It is often desirable that the non-secreted protein lack an activity possessed by the wild type non-secreted protein.

A "signal" or "signal sequence," as used herein, refers to an amino terminal sequence which directs the expression of a protein to the exterior of the cell or into a membrane. Preferred signal sequences are those from secreted proteins, more preferably protein which are secreted into the milk of a mammal.

GAD, as used herein, refers to glutamic acid decarboxylase. GAD produced by the GAD65 gene is preferred for use herein.

An "isolated" nucleic acid, as used herein, refers to a nucleic acid molecule which is free of sequences which naturally flank the nucleic acid (i.e., sequences located at the 5' and 3' ends of the nucleic acid) in the genomic DNA of the organism from which the nucleic acid is derived. Moreover, an "isolated" nucleic acid, such as a cDNA molecule, can be free of other cellular material.

As used herein, the phrase "non-secreted polypeptide," refers to a protein which is normally found in the nucleus or the cytoplasm of a cell and which is not normally found as a membrane protein or secreted through the membrane to be released outside the cell. Examples of such proteins include, but are not limited to, enzymes, transcription factors, cell cycle regulatory proteins, oncoproteins, ribosomal proteins, structural proteins, and cellular signal transduction proteins.

The terms "peptides", "proteins", and "polypeptides" are used interchangeably herein.

As used herein, a tolerogen, is a molecule which presents an epitope to an organism such that immunological tolerance is induced to the epitope. Tolerogens can be proteins.

As used herein, the term "operatively linked," refers to a DNA segment which is placed into a functional relationship with another DNA segment. For example, DNA for a signal sequence is operatively linked to DNA encoding a polypeptide if it participates in the secretion of the polypeptide; a promoter or enhancer is operatively linked to a coding sequence it is promotes the transcription of the sequence. Generally, DNA sequences that are operatively linked are contiguous, and in the case of a signal sequence both contiguous and in reading phase. However, enhancers need not be contiguous with the coding sequences whose transcription they control. Linking is accomplished by ligation at convenient restriction sites or at adapters or linkers inserted in lieu thereof.

As used herein, the term "heterologous polypeptide," refers to a protein or peptide coded for by a DNA sequence which is not endogenous to the native genome of the organism in which it is produced, e.g., a mammal in whose milk it is produced. The term also includes a protein or peptide coded for by a DNA sequence which if endogenous to the native genome of the mammal in whose milk it is produced does not lead to the natural production of that protein or peptide in its milk.

The term "subject," as used herein, is intended to include mammals having or being susceptible to an unwanted disease or a condition. Examples of such subjects include humans, dogs, cats, pigs, goats, cows, horses, rats and mice.

The term "treating a condition" is intended to include preventing, inhibiting, reducing, or delaying the progression of the condition.

The transgenically produced non-secreted polypeptides produced according to the invention find use in a wide variety of therapeutic procedures, such as in preparation of pharmaceutical compositions for administration to patients or in diagnosis of diseases. For example, transgenically produced GAD can be used for diagnosis and treatment of diabetes and transgenically produced MBP can be used in the treatment and diagnosis of multiple sclerosis.

The application of transgenic technology to the commercial production of recombinant proteins in the milk of transgenic animals using milk protein specific signal and promoter sequences offers significant advantages over traditional methods of non-secreted protein production. These advantages include a reduction in the total amount of required capital expenditures, elimination of the need for capital commitment to build facilities early in the product development life cycle, and lower direct production cost per unit for complex proteins. Of key importance is the likelihood that, for certain non-secreted proteins, transgenic production may represent the only technologically and economically feasible method of commercial production.

Myelin basic protein (MBP) is membrane associated protein synthesized by oligodendrocytes and Schwann cells. It is not secreted in its natural environment. MBP is also an autoantigen of the disease multiple sclerosis. Animal model studies and clinical trial data have suggested that administrating MBP orally could establish peripheral immune tolerance and thereby suppress the symptoms of the disease.

Glutamic acid decarboxylase (GAD), another cytoplasmic protein, is an enzyme that catalyzes the biosynthesis of the neurotransmitter, γ-aminobutyric acid. The human genome has at least two homologous genes located on chromosomes 2 and 10. The GAD65 and the GAD67 cDNA derived primary amino acid sequences are 65% identical, with the difference between the two isomers in the first 250 amino acids being approximately 75%. GAD65 has been recently identified as a critical β-cell autoantigen in the disease insulin-dependent diabetes mellitus. Experiments in the NOD mouse model of insulin-dependent diabetes mellitus have shown an early appearance of GAD65-reactive antibodies and T cells, and have demonstrated protection of diabetes by early GAD treatment, indicating that GAD65 is a key antigen in the disease process (Kaufman et al. *Nature* 366:69–72, 1993; Tisch et al. *Nature* 366:72–5, 1993). The presence of anti-GAD antibodies in the sera of prediabetic individuals can serve as reliable makers for progression to overt diabetes. GAD is, therefore, thought to be a candidate for tolerance therapy.

Current methods of obtaining glutamic acid decarboxylase involve purification from a natural sources such as human or non-human CNS or pancreatic cells (Ortel et al. *Brain Res. Bull.* 5(2):713–719, 1980; Ortel et al. *J. Neurosci.* 6:2689–2700, 1981); by preparing synthetic proteins based on the sequence, or by expression in cultured mammalian cells. However, the use of conventionally obtained GAD presents various problems due to the unavailability of large quantities of cells, expense associated with producing synthetic peptides and inability to secrete the recombinant protein in COS cells.

The methods described herein allow the production of high levels of secreted proteins which are not normally secreted, e.g., glutamic acid decarboxylase (GAD), a protein that is a potential therapy for insulin-dependent diabetes mellitus (Type 1 diabetes), in the milk of a transgenic animal.

The expression of GAD, a non-secreted protein, is a significant technical achievement. Proteins that are not normally secreted by cells are extremely difficult to produce as they remain with in the producing cell. In order to generate sufficient quantities of a non-secreted protein, like GAD, the producing cells must be harvested and the protein separated from the cells and other proteins found within those cells.

In a transgenic mammal, the protein is secreted by the mammary gland cells into the milk of the mammal.

The work herein shows the ability of transgenic technology to produce a broad and important class of proteins difficult to express in any other system.

The transgenic production of a non-secreted protein in milk provides a cost-effective method of producing high volumes needed for potential commercialization. In addition, since milk from dairy animals can be ingested by humans, this method is especially appropriate for use in oral tolerization.

Oral tolerance is a mechanism that allows the human body to regulate the immune system so that it can absorb foreign materials as nourishment. Preclinical and clinical observations of oral tolerance show that digesting certain proteins can suppress autoimmune diseases such as rheumatoid arthritis and multiple sclerosis.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. : 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

Other features and advantages of the invention will be apparent from the following detailed description, and from the claims.

BRIEF DESCRIPTION OF THE INVENTION

The drawings will first be briefly described.

Drawings.

This invention is based upon the discovery that naturally non-secreted polypeptides, e.g., GAD or MBP, produced by the transgenic method of the present invention can be secreted in the milk of transgenic mammals.

The method of the invention demonstrates a strategy that leads to the efficient secretion of normally non-secreted proteins, e.g., truncated, cytoplasmic or nuclear proteins, in the milk of transgenic mammals. It has been demonstrated herein that adding a goat β-casein signal peptide, or β-casein signal peptide and the N-terminal portion of β-casein, to the N-terminal portion of MBP and GAD is sufficient to secrete these normally cytoplasmic proteins in the milk of transgenic mice. Thus, the method of the invention facilitates the production of normally non-secreted proteins, as well as truncated polypeptides, in the milk of transgenic mammals.

Milk Specific Promoters

The transcriptional promoters useful in practicing the present invention are those promoters that are preferentially activated in mammary epithelial cells, including promoters that control the genes encoding milk proteins such as caseins, beta lactoglobulin (Clark et al., (1989) *Bio/Technology* 7: 487–492), whey acid protein (Gorton et al. (1987) *Bio/Technology* 5: 1183–1187), and lactalbumin (Soulier et al., (1992) *FEBS Letts*. 297: 13). Casein promoters may be derived from the alpha, beta, gamma or kappa casein genes of any mammalian species; a preferred promoter is derived from the goat beta casein gene (DiTullio, (1992) *Bio/Technology* 10:74–77). The milk-specific protein promoter or the promoters that are specifically activated in mammary tissue may be derived from either cDNA or genomic sequences. Preferably, they are genomic in origin.

DNA sequence information is available for all of the mammary gland specific genes listed above, in at least one, and often several organisms. See, e.g., Richards et al., *J. Biol. Chem.* 256, 526–532 (1981) (α-lactalbumin rat); Campbell et al., *Nucleic Acids Res.* 12, 8685–8697 (1984) (rat WAP); Jones et al., *J. Biol. Chem.* 260, 7042–7050 (1985) (rat β-casein); Yu-Lee & Rosen, *J. Biol. Chem.* 258, 10794–10804 (1983) (rat γ-casein); Hall, *Biochem. J.* 242, 735–742 (1987) (α-lactalbumin human); Stewart, *Nucleic Acids Res.* 12, 389 (1984) (bovine αs1 and κ casein cDNAs); Gorodetsky et al., *Gene* 66, 87–96 (1988) (bovine β casein); Alexander et al., *Eur. J. Biochem.* 178, 395–401 (1988) (bovine κ casein); Brignon et al., *FEBS Lett.* 188, 48–55 (1977) (bovine αS2 casein); Jamieson et al., *Gene* 61, 85–90 (1987), Ivanov et al., *Biol. Chem.* Hoppe-Seyler 369, 425–429 (1988), Alexander et al., *Nucleic Acids Res.* 17, 6739 (1989) (bovine β lactoglobulin); Vilotte et al., *Biochimie* 69, 609–620 (1987) (bovine α-lactalbumin). The structure and function of the various milk protein genes are reviewed by Mercier & Vilotte, *J. Dairy Sci*. 76, 3079–3098 (1993) (incorporated by reference in its entirety for all purposes). To the extent that additional sequence data might be required, sequences flanking the regions already obtained could be readily cloned using the existing sequences as probes. Mammary-gland specific regulatory sequences from different organisms are likewise obtained by screening libraries from such organisms using known cognate nucleotide sequences, or antibodies to cognate proteins as probes.

Signal Sequences

Among the signal sequences that are useful in accordance with this invention are milk-specific signal sequences or other signal sequences which result in the secretion of eukaryotic or prokaryotic proteins. Preferably, the signal sequence is selected from milk-specific signal sequences, i.e., it is from a gene which encodes a product secreted into milk. Most preferably, the milk-specific signal sequence is related to the milk-specific promoter used in the expression system of this invention. The size of the signal sequence is not critical for this invention. All that is required is that the sequence be of a sufficient size to effect secretion of the desired recombinant protein, e.g., in the mammary tissue. For example, signal sequences from genes coding for caseins, e.g., alpha, beta, gamma or kappa caseins, beta lactoglobulin, whey acid protein, and lactalbumin are useful in the present invention. The preferred signal sequence is the goat β-casein signal sequence.

Signal sequences from other secreted proteins, e.g., proteins secreted by liver cells, kidney cell, or pancreatic cells can also be used.

Amino-Terminal Regions of Secreted Proteins

The efficacy with which a non-secreted protein is secreted can be enhanced by inclusion in the protein to be secreted all or part of the coding sequence of a protein which is normally secreted. Preferably the entire sequence of the protein which is normally secreted is not included in the sequence of the protein but rather only a portion of the amino terminal end of the protein which is normally secreted. For example, a protein which is not normally secreted is fused (usually at its amino terminal end) to an amino terminal portion of a protein which is normally secreted.

Preferably, the protein which is normally secreted is a protein which is normally secreted in milk. Such proteins include proteins secreted by mammary epithelial cells, milk proteins such as caseins, beta lactoglobulin, whey acid protein, and lactalbumin. Casein proteins include alpha, beta, gamma or kappa casein genes of any mammalian species. A preferred protein is beta casein, e.g., a goat beta casein. The sequences which encode the secreted protein can be derived from either CDNA or genomic sequences. Preferably, they are genomic in origin, and include one or more introns.

DNA Constructs

The expression system or construct, described herein, can also include a 3' untranslated region downstream of the DNA sequence coding for the non-secreted protein. This region apparently stabilizes the RNA transcript of the expression system and thus increases the yield of desired protein from the expression system. Among the 3' untranslated regions useful in the constructs of this invention are sequences that provide a poly A signal. Such sequences may be derived, e.g., from the SV40 small t antigen, the casein 3' untranslated region or other 3' untranslated sequences well known in the art. Preferably, the 3' untranslated region is derived from a milk specific protein. The length of the 3' untranslated region is not critical but the stabilizing effect of its poly A transcript appears important in stabilizing the RNA of the expression sequence.

Optionally, the expression system or construct includes a 5' untranslated region between the promoter and the DNA sequence encoding the signal sequence. Such untranslated regions can be from the same control region from which promoter is taken or can be from a different gene, e.g., they may be derived from other synthetic, semi-synthetic or natural sources. Again their specific length is not critical, however, they appear to be useful in improving the level of expression.

The construct can also include about 10%, 20%, 30%, or more of the N-terminal coding region of the gene preferentially expressed in mammary epithelial cells. For example, the N-terminal coding region can correspond to the promoter used, e.g., a goat β-casein N-terminal coding region.

The above-described expression systems may be prepared using methods well known in the art. For example, various ligation techniques employing conventional linkers, restriction sites etc. may be used to good effect. Preferably, the expression systems of this invention are prepared as part of larger plasmids. Such preparation allows the cloning and selection of the correct constructions in an efficient manner as is well known in the art. Most preferably, the expression systems of this invention are located between convenient restriction sites on the plasmid so that they can be easily isolated from the remaining plasmid sequences for incorporation into the desired mammal.

Prior art methods often include making a construct and testing it for the ability to produce a product in cultured cells prior to placing the construct in a transgenic animal. Surprisingly, the inventors have found that such a protocol may not be of predictive value in determining if a normally non-secreted protein can be secreted, e.g., in the milk of a transgenic animal. Therefore, it may be desirable to test constructs directly in transgenic animals, e.g., transgenic mice, as some constructs which fail to be secreted in CHO cells are secreted into the milk of transgenic animals.

Transzenic Mammals

The DNA constructs of the invention are introduced into the germ line of a mammal. For example, one or several copies of the construct may be incorporated into the genome of a mammalian embryo by standard transgenic techniques.

Any non-human mammal can be usefully employed in this invention. Mammals are defined herein as all animals, excluding humans, that have mammary glands and produce milk. Preferably, mammals that produce large volumes of milk and have long lactating periods are preferred. Preferred mammals are cows, sheep, goats, mice, oxen, camels and pigs. Of course, each of these mammals may not be as effective as the others with respect to any given expression sequence of this invention. For example, a particular milk-specific promoter or signal sequence may be more effective in one mammal than in others. However, one of skill in the art may easily make such choices by following the teachings of this invention.

One technique for transgenically altering a mammal is to microinject the construct into the pronuclei of the fertilized mammalian egg(s) to cause one or more copies of the construct to be retained in the cells of the developing mammal(s). Usually, at least 40% of the mammals developing from the injected eggs contain at least one copy of the cloned construct in somatic tissues and these "transgenic mammals" usually transmit the gene through the germ line to the next generation. The progeny of the transgenically manipulated embryos may be tested for the presence of the construct by Southern blot analysis of the segment of tissue. If one or more copies of the exogenous cloned construct remains stably integrated into the genome of such transgenic embryos, it is possible to establish permanent transgenic mammal lines carrying the transgenically added construct.

The litters of transgenically altered mammals may be assayed after birth for the incorporation of the construct into the genome of the offspring. Preferably, this assay is accomplished by hybridizing a probe corresponding to the DNA sequence coding for the desired recombinant protein product or a segment thereof onto chromosomal material from the progeny. Those mammalian progeny found to contain at least one copy of the construct in their genome are grown to maturity. The female species of these progeny will produce the desired protein in or along with their milk. Alternatively, the transgenic mammals may be bred to produce other transgenic progeny useful in producing the desired proteins in their milk.

Transgenic females may be tested for protein secretion into milk, using any of the assay techniques that are standard in the art (e.g., Western blots or enzymatic assays).

Pharmaceutical Compositions

Preferred pharmaceutical compositions for inducing tolerance to proteins include the appropriate tolerogen in the milk of a transgenic animal.

Transgenically produced non-secreted polypeptide of the invention can be incorporated into pharmaceutical compositions useful to attenuate, inhibit, or prevent a disease or a disorder, e.g., the destruction of pancreatic β-cells associated with the onset of insulin-dependent diabetes mellitus, or the autoimmunity associated with multiple sclerosis. The compositions should contain a therapeutic or prophylactic amount of the transgenically produced non-secreted polypeptide, e.g., GAD or MBP, in a pharmaceutically-acceptable carrier or in the milk of the transgenic animal. The pharmaceutical carrier can be any compatible, non-toxic substance suitable to deliver the polypeptides to the patient. Sterile water, alcohol, fats, waxes, and inert solids may be used as the carrier. Pharmaceutically-acceptable adjuvants, buffering agents, dispersing agents, and the like, may also be incorporated into the pharmaceutical compositions. The concentration of the transgenically produced non-secreted peptide or other active agent in the pharmaceutical composition can vary widely, i.e., from less than about 0.1% by weight, usually being at least about 1% weight to as much as 20% by weight or more.

For oral administration, the active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

For nasal administration, the polypeptides can be formulated as aerosols. The term "aerosol" includes any gas-borne suspended phase of the compounds of the instant invention which is capable of being inhaled into the bronchioles or nasal passages. Specifically, aerosol includes a gas-borne suspension of droplets of the compounds of the instant invention, as may be produced in a metered dose inhaler or nebulizer, or in a mist sprayer. Aerosol also includes a dry powder composition of a compound of the instant invention suspended in air or other carrier gas, which may be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273–313; and Raeburn et al. (1992) *J. Pharmacol. Toxicol. Methods* 27:143–159.

The pharmaceutical compositions of the present invention are usually administered intravenously or orally. Intradermal or intramuscular administration is also possible in some circumstances. The compositions can be administered for prophylactic treatment of individuals suffering from, or at risk of a disease or a disorder, e.g., IDDM or multiple sclerosis. For therapeutic applications, the pharmaceutical compositions are administered to a patient suffering from established diabetes in an amount sufficient to inhibit or prevent further β-cell destruction. For individuals at risk of IDDM or multiple sclerosis, the pharmaceutical compositions are administered prophylactically in an amount sufficient to either prevent or inhibit immune destruction. An amount adequate to accomplish this is defined as a "therapeutically-effective dose."

Production of Non-secreted Protein Variants (Non Wild-type Proteins)

Production of Altered DNA and Peptide Sequences: Random Methods

Amino acid sequence variants of a protein can be prepared by random mutagenesis of DNA which encodes a protein or a particular domain or region of a protein. Useful methods include PCR mutagenesis and saturation mutagenesis. A library of random amino acid sequence variants can also be generated by the synthesis of a set of degenerate oligonucleotide sequences.

PCR Mutagenesis

In PCR mutagenesis, reduced Taq polymerase fidelity is used to introduce random mutations into a cloned fragment of DNA (Leung et al., 1989, *Technique* 1:11–15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complimentary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, SA (1983) *Tetrahedron* 39:3; Itakura et al. (1981) *Recombinant DNA, Proc 3rd Cleveland Sympos. Macromolecules*, ed. AG Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Production of Altered DNA and Peptide Sequences: Methods for Directed Mutagenesis Non-random or directed, mutagenesis techniques can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1–3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081–1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (DNA 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci. USA*, 75: 5765[1978]).

Cassette Mutagenesis

Another method for preparing variants, cassette mutagenesis, is based on the technique described by Wells et al. (*Gene*, 34:315[1985]). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants (Ladner et al., WO 88/06630). In this method, the amino acid sequences for a group of homologs or other related proteins are aligned, preferably to promote the highest homology possible. All of the amino acids which appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

This invention is further illustrated by the following examples which in no way should be construed as being further limiting. The contents of all cited references (including literature references, issued patents, published patent applications, and co-pending patent applications) cited throughout this application are hereby expressly incorporated by reference.

EXAMPLES

1. Cloning of β-casein-MBP Fusion Gene

Figure 1A:
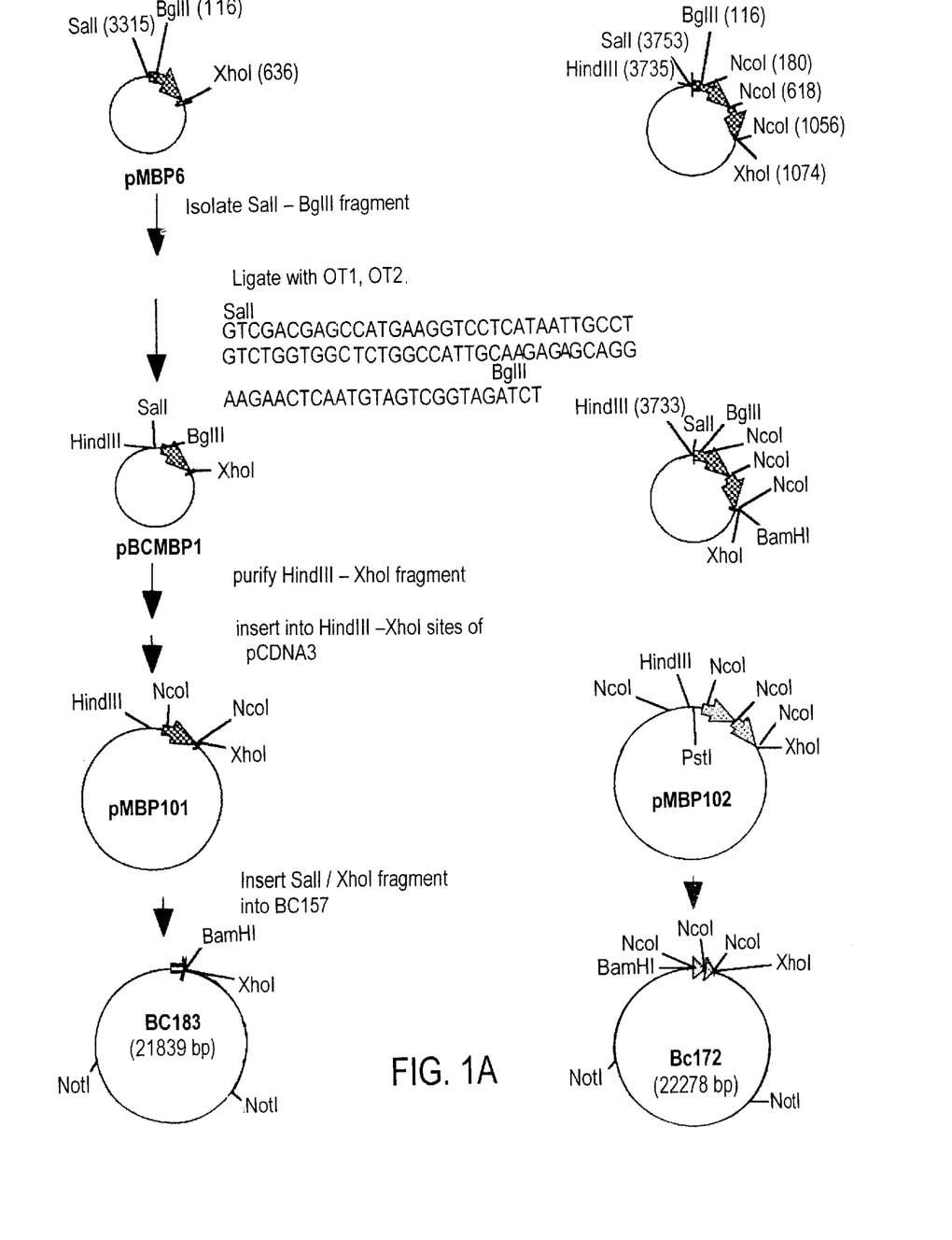
FIG. 1 is a schematic diagram of the construction of the β-casein/MBP fusion gene.
Figure 1B:
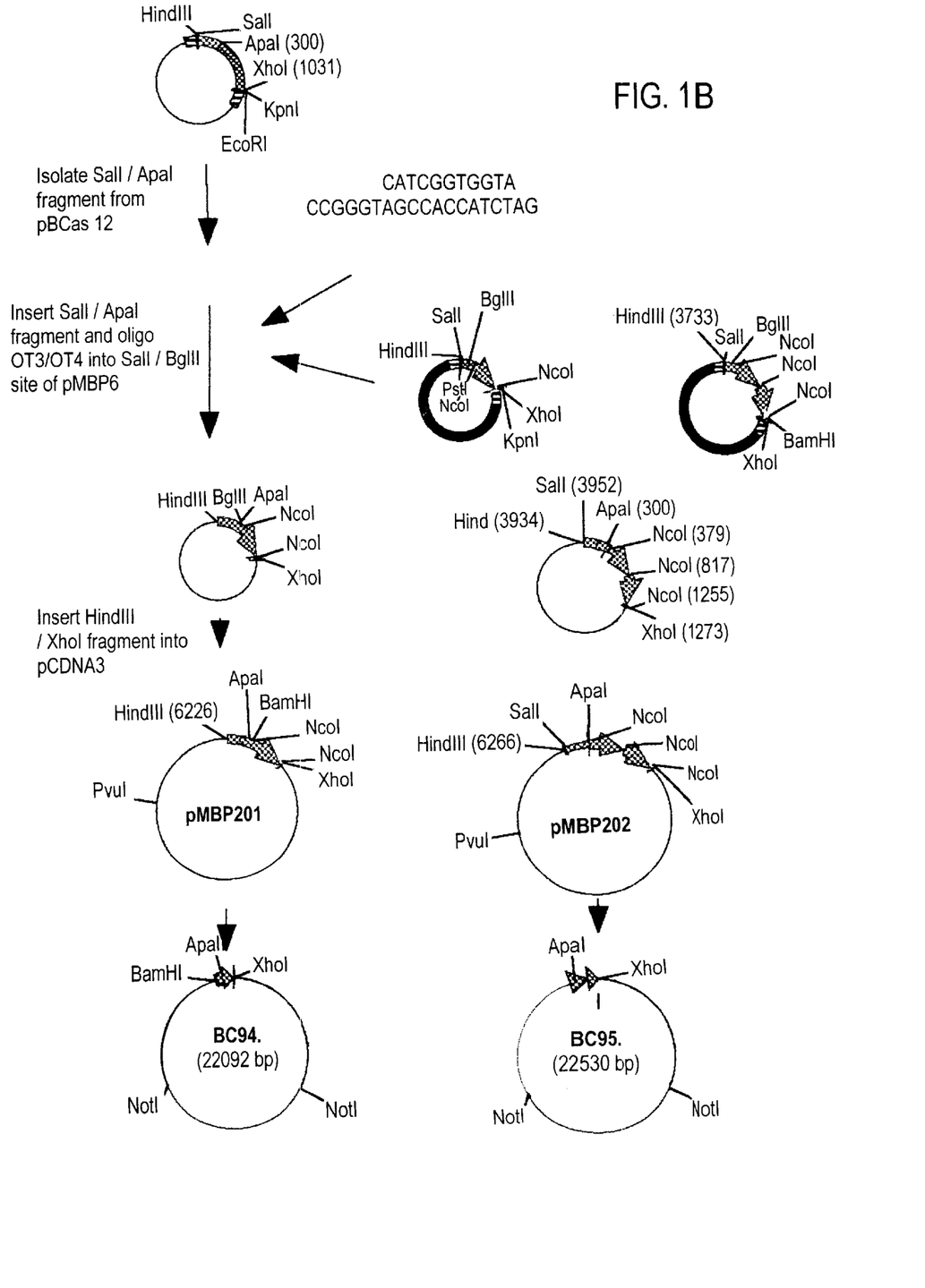

Five plasmids containing the β-casein/MBP fusing gene were constructed. As depicted in FIG. 1, plasmid pBCMBP1 was generated by ligating goat β-casein signal sequences (oligos OT1 AND OT2) to SalI/BglII sites of pMBP6. Cloning the HindIII-XhoI fragment of pBCMBP1 into pCDNA3 generated pBCMBP101. Plasmid pBCMBP102 was generated by inserting an additional NcoI fragment pMBP6 into the NcoI site of pBCMBP101. SalI/XhoI fragments of pBCMBP101, pBCMBP102 were inserted into BC157 to generated BC183 and BC172, respectively.

Plasmid pBCMBP2 was generated by ligating SalI-ApaI fragment of pBC12 (which contains β-casein signal sequence and 30% of the N-terminal coding region of goat β-casein) and a pair of adapter oligos (oligos OT3 and OT4) into the SalI-BglII site of pMBP6. The HindIII/EcoRI fragment of the pBCMBP2, which carries sequences encoding the β-casein signal and N terminal portion followed by the entire MBP coding region was cloned into pCDNA3 to yield pBCMBP201. Plasmid pBCMBP202 was generated by inserting an additional NcoI fragment of pMBP6 into the NcoI site of pBCMBP201. SalI/XhoI fragments of pBCMBP201, pBCMBP202 were inserted into BC157 to generated BC94 and BC95, respectively.

To construct MBP and tPA signal sequence, polymerase chain reaction was used to obtain a MBP cDNA fragment with oligos MBP1 and MBP2. The PCR fragment was digested with BglII/XhoI and cloned into BglII/XhoI digested pUCsigtPA, which contains the human LatPA signal sequence. The new plasmid, designated pMBP6, contained a fusion gene with tPA signal fused to MBP coding region. SalI/XhoI fragment from pMBP6 was cloned into the mammary expression vector BC163 to generate BC60.

Oligos Used

OT 1, TCG ACG AGA GCC ATG AAG GTC CTC ATC CTT GCC TGT CTG GTG GCT CTG CGG ATT GCA AGA GAG CAG GAA GAA CTC AAT GTA GTC GGT A (SEQ ID NO:1)

OT 2, GAT CTA CCG ACT ACA TTG AGT TCT TCC TGC TCT CTT GCA ATG GCC AGA GCC ACC AGA CAG GCA AGG ATG AGG ACC TTC ATG GCT CTC G (SEQ ID NO:2)

OT 3, GAT CGG TGG TA (SEQ ID NO:3)

OT 4, GAT CTA CCA CCG ATG GGC C (SEQ ID NO:4)

MBP 1, CCA TTG CAA GAT CTG CGT CAC AGA AGA GAC CCT CC (SEQ ID NO:5)

MBP 2, TCA CCC ATG GCT AGA CGC TGA CTC GAG GAT CCT TGT CA (SEQ ID NO:6)

2. Secretion of MBP) MBP Fusion Proteins in Tissue Culture

To determine if the cytoplasmic protein MBP can be secreted by adding tPA or β-casein signal peptides plasmids pMBP6, pBCMBP101, pBCMBP102, pBCMBP201 and pBCMBP202 were first transfected into COS-7 cells. Northern analysis revealed that mRNA for all these MBP constructs was expressed in tissue culture following transient transfection. When the transfected COS cells were analyzed by immunoprecipitation for protein secretion, it was found that only the tPA signal peptide sequence (pMBP6) failed to secrete MBP. MBP with the β-casein fusion proteins (pBCMBP201, pBCMBP202) were all secreted in tissue culture.

3. Cloning of the GAD-Casein Fusion Genes

To further demonstrate that fusion to β-casein signal peptide is a reliable method to direct the secretion of non-secreted protein into the milk of the transgenic animals, the similar strategy was employed to secrete another non-secreted cytoplasmic protein, the glutamic acid decarboxylase (GAD).

To secrete GAD, the following fusion genes were constructed:

1. Human GAD cDNA fused to goat β-casein signal sequence. The fusion gene inserted in the expression vector pCDNA3 was designated as huGAD7. This plasmid was constructed by ligating a pair of oligo (OT1 and OT2) that encode the β-casein signal sequence flanked by SalI/BglII sites, a BglII/NcoI adapter, and a NcoI/XhoI fragment of huGAD 1, which encode the wild type GAD, into the XhoI site of the expression vector pCDNA3.

2. Human GAD cDNA with a point mutation (PLP mutation) that knocks out the decarboxylase activity, was fused to goat β-casein signal sequence. The fusion gene inserted in the expression vector pCDNA3 was designated as huGAD8. This plasmid was constructed by ligating oligo OT1 and OT2, a BglII/NcoI adapter, and a NcoI/XhoI fragment of huGAD2, which encode the mutated GAD, into the XhoI site of the expression vector pCDNA3.

Figure 2:
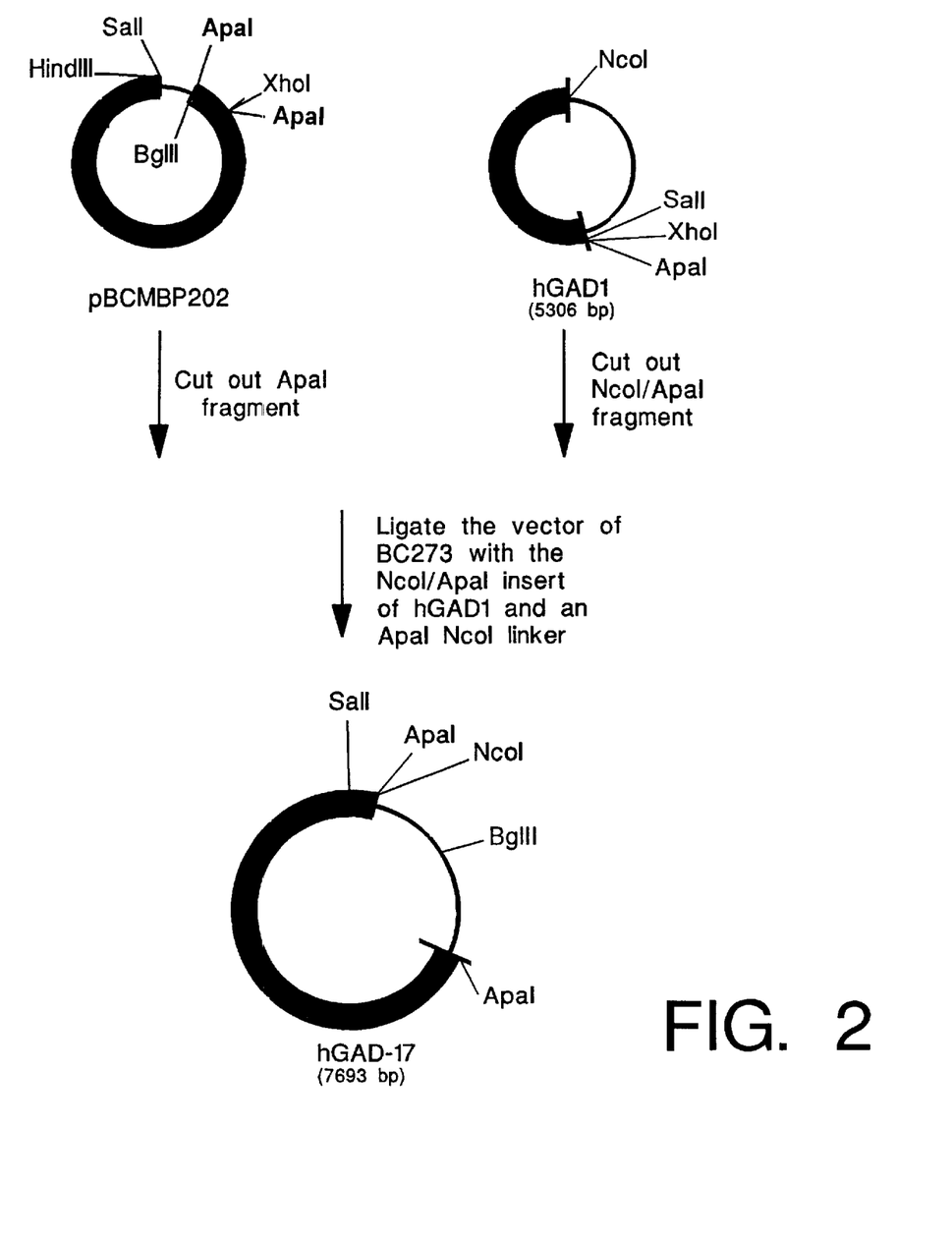
FIG. 2 is a schematic diagram of the construction of the hGAD-17 fusion gene.

3. hGAD cDNA was fused to goat β-casein signal sequence and an N-terminal portion of goat β-casein coding sequence. The fusion gene inserted in the expression vect or pCDNA3 was designated as huGAD17. The construction of this plasmid is illustrated in FIG. 2.

Figure 3:
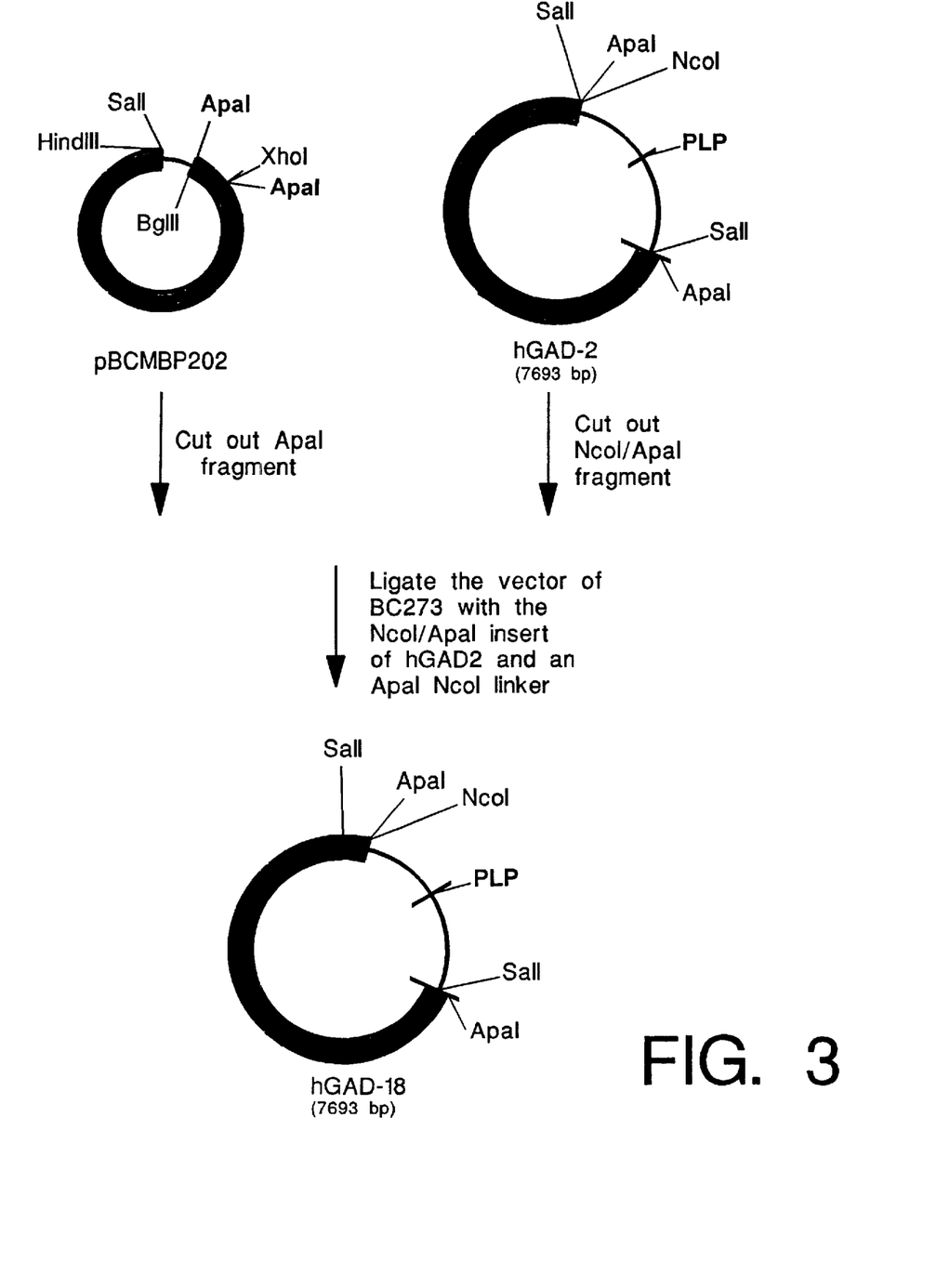
FIG. 3 is a schematic diagram of the construction of the hGAD-18 fusion gene.

4. hGAD cDNA with PLP mutation was fused to goat β-casein signal sequence and an N-terminal portion of goat β-casein coding sequences. The fusion gene inserted in the expression vector pCDNA3 was designated as huGAD 18. The construction of this plasmid is illustrated in FIG. 3.

5. A pair of control GAD constructs (both wild type and mutant) that lack any signal sequences, were cloned into pCDNA3. The plasmids were designated, respectively, as huGAD9, for wild type GAD, and huGAD10, for GAD with the PLP mutation.

4. Expression of GAD-casein Fusion Protein in Tissue Culture

Cultured COS-7 cells were transfected with huGAD7, huGAD8, huGAD17, huGAD 18, huGAD9, huGAD 10, and the expression of the GAD or GAD-casein fusion proteins were examined by Northern blotting of total RNA isolated from transfected COS cells and by immunoprecipitation of $^{35}$S labeled medium and lysates of the transfected COS cells with a polyclonal anti-GAD antiserum. The results from the Northern blotting indicated that the mRNA was transcribed from all these constructs. Immunoprecipitation of the metabolically labeled transfected COS cells indicated that 1) GAD or GAD-casein fusion proteins were synthesized from all of the constructs, because they can be readily detected in the lysate fraction; 2) GAD or GAD-casein fusion protein was not detected in the media fraction. Only residual amount of GAD or GAD-casein fusion proteins was detected in the culture media, which was most likely the result of nonspecific lysis of the COS cells. There was no significant difference between the control constructs, huGAD9 and huGAD 10, that lack the signal sequence and the constructs huGAD7, huGAD8, huGAD17 and huGAD18 in the level and pattern of GAD expression. These results suggested that the GAD or GAD-casein fusion protein was not secreted by COS cells.

5. Testing and Characterization of Gene Constructs in Transgenic Mice

Transgene constructs are generally tested in a mouse model system to assess their ability to direct high levels of expression and their ability to express in a tissue-specific manner.

Transgenic mice were generated by injecting mouse embryos with DNA fragments prepared by BC60, BC183, BC94, BC172, and BC192. Analysis of the milk of the female transgenic mice revealed that while the tPA signal peptide failed to secrete MBP into the milk (BC60), MBP with the β-casein signal peptide (BC183, BC172), as well as MBP/β-casein fusion protein (BC94) were expressed by the mouse mammary epithelial cell and secreted into the milk. When milk from the BC94 line (MBP/β-casein fusion) was analyzed by SDS PAGE followed by Coomassie staining, an additional protein was found to be present in the milk of transgenic mouse lines 94-1-106 and 94-2-167. Furthermore, when a duplicate SDS PAGE was subjected to Western analysis, this additional protein was found to be immunologically reactive to antibodies against MBP, confirming that the MBP/β-casein fusion protein is secreted into the milk. The level of MBP fusion expression in the milk of the BC94-1-106 line was estimated to be 4 mg/ml.

To access if GAD-casein fusion protein can be secreted by the mammary epithelial cells, the coding sequence of hGAD 18 was excised as a SalI/XhoI fragment and subcloned into the XhoI site of the β-casein expression vector BC350 to yield construct BC433. Transgenic mice were generated by microinjecting the SalI/NotI fragment of BC433 into the mouse embryos. Fourteen lines of transgenic mice were established. Western analysis of the milk of the GAD transgenic mice using monoclonal anti-GAD antibody showed that five of the six lines expressed GAD-casein fusion protein in the milk. The concentration of the GAD in milk of the highest expressor, BC433–208, was 8 mg/ml.

To access if the wild type GAD-casein fusion protein can be expressed in transgenic mice by mammary epithelial cells, the coding sequence of hGAD 18 was excised as a Sal I/Xho I fragment and subcloned into the Xho I site of β-casein expression vector BC350 to yield plasmid BC569. Transgenic mice were generated by microinjecting the Sal I/Not I fragment of BC569 into the mouse embryos. Eleven lines of transgenic mice were established. Western analysis of the milk collected from these transgenic mice using monoclonal anti-GAD antibody showed that the wild type GAD-casein fusion protein was expressed at the levels of 4 mg/ml.

To access if the 15 amino acid β-casein signal peptide is by itself sufficient to secrete GAD into the milk of transgenic mice, a plasmid was constructed by fusing oligos which encode the 15 amino acid β-casein signal peptide directly to the GAD cDNA. Consequently, if the signal peptide is recognized and processed, this construct should lead to the secretion of natural GAD into milk, instead of GAD with 67 extra amino acids fused to its N-terminal, as is the case with BC569 construct. The plasmid was constructed by ligating oligos OT9 (TCG AGC CCA CCA TGA AGG TCC TCA TCC TTG CCT GTC TGG TGG CTC TGG CCA TTG (SEQ ID NO:7)) and OT10 (CAT GGC AAT GGC CAG AGC CAC CAG ACA GGC AAG GAT GAG GAC CTT CAT GGT GGC (SEQ ID NO:8)) and a Sal I/Nco I GAD fragment of huGAD 17 into the Xho I site of the β-casein expression vector BC350. This yielded the BC577 construct. A Sal I/Xho I fragment of BC577 was microinjected into the mouse embryo to generate transgenic mice. Twenty two transgenic lines were established. Western analysis of the milk collected from the female transgenic mice showed GAD expression of 4 mg/ml.

6. Generation and Characterization of Transgenic Animals

A founder ($F_o$) transgenic goat is defined as a viable transgenic animal resulting from embryo transfer of fertilized goat eggs that have been microinjected with a specified construct (e.g., BC433, BC569, BC577, or BC94). The general methodologies that follow in this section can be used to generate all transgenic goats.

Goat Species and Breeds:
The transgenic goats produced for non-secreted protein, e.g., GAD or MBP, production can be of Swiss origin, and are the Alpine, Saanen, and Toggenburg breeds.

Goat Superovulation:
The timing of estrus in the donors are synchronized on Day 0 by 6 mg subcutaneous norgestomet ear implants (Syncromate-B, CEV A Laboratories, Inc., Overland Park, Kans.). Prostaglandin is administered after the first seven to nine days to shut down the endogenous synthesis of progesterone. Starting on Day 13 after insertion of the implant, a total of 18 mg of follicle-stimulating hormone (FSH-Schering Corp., Kenilworth, N.J.) is given intramuscularly over three days in twice-daily injections. The implant is removed on Day 14. Twenty-four hours following implant removal the donor animals are mated several times to fertile males over a two-day period (Selgrath, et al., Theriogenology, 1990. pp. 1195–1205).

Embryo Collection:
Surgery for embryo collection occurs on the second day following breeding (or 72 hours following implant removal). Superovulated does are removed from food and water 36 hours prior to surgery. Does are administered 0.8 mg/kg Diazepam (Valium®), IV, followed immediately by 5.0 mg/kg Ketamine (Keteset), IV. Halothane (2.5%) is administered during surgery in 2 L/min oxygen via an endotracheal tube. The reproductive tract is exteriorized through a midline laparotomy incision. Corpora lutea, unruptured follicles greater than 6 mm in diameter, and ovarian cysts are counted to evaluate superovulation results and to predict the number of embryos that should be collected by oviductal flushing. A cannula is placed in the ostium of the oviduct and held in place with a single temporary ligature of 3.0 Prolene. A 20 gauge needle is placed in the uterus approximately 0.5 cm from the uterotubal junction. Ten to twenty ml of sterile phosphate buffered saline (PBS) is flushed through the cannulated oviduct and collected in a Petri dish. This procedure is repeated on the opposite side and then the reproductive tract is replaced in the abdomen. Before closure, 10–20 ml of a sterile saline glycerol solution is poured into the abdominal cavity to prevent adhesions. The linea alba is closed with simple interrupted sutures of 2.0 Polydioxanone or Supramid and the skin closed with sterile wound clips.

Fertilized goat eggs are collected from the PBS oviductal flushings on a stereomicroscope, and are then washed in Ham's F12 medium (Sigma, St. Louis, Mo.) containing 10% fetal bovine serum (FBS) purchased from Sigma. In cases where the pronuclei are visible, the embryos is immediately microinjected. If pronuclei are not visible, the embryos are placed in Ham's F12 containing 10% FBS for short term culture at 37° C. in a humidified gas chamber containing 5% $CO_2$ in air until the pronuclei become visible (Selgrath, et al., Theriogenology, 1990. pp. 1195–1205).

Microinjection Procedure
One-cell goat embryos are placed in a microdrop of medium under oil on a glass depression slide. Fertilized eggs having two visible pronuclei are immobilized on a flame-polished holding micropipet on a Zeiss upright microscope with a fixed stage using Normarski optics. A pronucleus is microinjected with the DNA construct of interest egg., BC433, BC569, BC577, or BC94, in injection buffer (Tris-EDTA) using a fine glass microneedle (Selgrath, et al., Theriogenology, 1990. pp. 1195–1205).

Embryo Development:
After microinjection, the surviving embryos are placed in a culture of Ham's F12 containing 10% FBS and then incubated in a humidified gas chamber containing 5% CO2 in air at 37° C. until the recipient animals are prepared for embryo transfer (Selgrath, et al., Theriogenology, 1990. p. 1195–1205).

Preparation of Recipients:

Estrus synchronization in recipient animals is induced by 6 mg norgestomet ear implants (Syncromate-B). On Day 13 after insertion of the implant, the animals are given a single non-superovulatory injection (400 I.U.) of pregnant mares serum gonadotropin (PMSG) obtained from Sigma. Recipient females are mated to vasectomized males to ensure estrus synchrony (Selgrath, et al., Theriogenology, 1990. pp. 1195–1205).

Embryo Transfer:

All embryos from one donor female are kept together and transferred to a single recipient when possible. The surgical procedure is identical to that outlined for embryo collection outlined above, except that the oviduct is not cannulated, and the embryos are transferred in a minimal volume of Ham's F12 containing 10% FBS into the oviductal lumen via the fimbria using a glass micropipet. Animals having more than six to eight ovulation points on the ovary are deemed unsuitable as recipients. Incision closure and post-operative care are the same as for donor animals (Selgrath, et al., Theriogenology, 1990. pp. 1195–1205).

Monitoring of Pregnancy and Parturition:

Pregnancy is determined by ultrasonography 45 days after the first day of standing estrus. At Day 110 a second ultrasound exam is conducted to confirm pregnancy and assess fetal stress. At Day 130 the pregnant recipient doe is vaccinated with tetanus toxoid and Clostridium C&D. Selenium and vitamin E (Bo-Se) are given IM and Ivermectin was given SC. The does are moved to a clean stall on Day 145 and allowed to acclimatize to this environment prior to inducing labor on about Day 147. Parturition is induced at Day 147 with 40 mg of PGF2a (Lutalyse®) purchased from Upjohn Company, Kalamazoo Mich. This injection is given IM in two doses, one 20 mg dose followed by a 20 mg dose four hours later. The doe is under periodic observation during the day and evening following the first injection of Lutalyse® on Day 147. Observations are increased to every 30 minutes beginning on the morning of the second day. Parturition occurred between 30 and 40 hours after the first injection. Following delivery the doe is milked to collect the colostrum and passage of the placenta is confirmed.

Verification of the Transgenic Nature of $F_0$ Animals:

To screen for transgenic $F_0$ animals, genomic DNA is isolated from two different cell lines to avoid missing any mosaic transgenics. A mosaic animal is defined as any goat that does not have at least one copy of the transgene in every cell. Therefore, an ear tissue sample (mesoderm) and blood sample are taken from a two day old $F_0$ animal for the isolation of genomic DNA (Lacy, et al., A Laboratory Manual, 1986, Cold Springs Harbor, N.Y.; and Herrmann and Frischauf, Methods Enzymology, 1987. 152: pp. 180–183). The DNA samples are analyzed by the polymerase chain reaction (Gould, et al., Proc. Natl. Acad. Sci, 1989. 86:pp. 1934–1938) using primers specific for GAD or MBP and by Southern blot analysis (Thomas, Proc Natl. Acad. Sci., 1980. 77:5201–5205) using a random primed GAD or MBP cDNA probe (Feinberg and Vogelstein, Anal. Bioc., 1983. 132: pp. 6–13). Assay sensitivity is estimated to be the detection of one copy of the transgene in 10% of the somatic cells.

Generation and Selection of Production Herd

The procedures described above are utilized for production of the transgenic founder ($F_0$) goats, as well as other transgenic goats. The transgenic $F_0$ founder goats, for example, are bred to produce milk, if female, or to produce a transgenic female offspring if it is a male founder.

This transgenic founder male, is bred to non-transgenic females, to produce transgenic female offspring.

Transmission of Transgene and Pertinent Characteristics

Transmission of the transgene of interest, e.g., GAD or MBP, in the goat line is analyzed in ear tissue and blood by PCR and Southern blot analysis. For example, Southern blot analysis of the founder male and the three transgenic offspring shows no rearrangement or change in the copy number between generations. The Southern blots are probed with the non-secreted protein, e.g., GAD or MBP, cDNA probe. The blots are analyzed on a Betascope 603 and copy number determined by comparison of the transgene to the goat beta casein endogenous gene.

Evaluation of Expression Levels

The expression level of the recombinant non-secreted protein, e.g., hGAD or hMBP, in the milk of transgenic animals is determined using enzymatic assays or Western blots.

Equivalents

Those skilled in the art will be able to recognize, or be able to ascertain using no more than routine experimentation, numerous equivalents to the specific procedures described herein. Such equivalents are considered to be within the scope of this invention and are covered by the following claims.

What is claimed is:

1. A method of making and secreting a non-secreted protein comprising: introducing into a mammal selected from the group consisting of sheep, mice, pigs, cows, rabbits and goats a nucleic acid construct which comprises:
   (a) a mammary epithelial specific promoter;
   (b) a milk protein specific signal sequence which can direct the secretion of a protein;
   (c) a sequence other than a signal sequence which encodes a sufficient portion of the amino terminal coding region from the amino terminal end of a milk protein to allow secretion in the milk of a transgenic mammal of a non-secreted protein; and
   (d) a sequence which encodes a non-secreted protein,
   wherein elements (a), (b), (c), and (d) are operatively linked in the order recited;
   expressing the protein, thereby producing the non-secreted protein in the milk of the transgenic mammal.

2. The method of claim 1, wherein the mammary epithelial specific promoter is the β-casein promoter sequence.

3. The method of claim 1, wherein the milk protein specific signal sequence is the β-casein signal sequence.

4. The method of claim 1, wherein the sequence encoding the non-secreted protein is of a human origin.

5. The method of claim 1, wherein the sequence encoding the non-secreted protein codes for a truncated, nuclear, or a cytoplasmic polypeptide.

6. The method of claim 1, wherein the sequence encoding the non-secreted protein codes for glutamic acid decarboxylase or myelin basic protein.

7. The method of claim 1, wherein the milk protein is β-casein.

8. The method of claim 1, wherein the amino terminal coding region comprises about 10% to 30% of the amino terminal coding region of a milk protein.

9. A method for providing a non-secreted protein in the milk of a transgenic mammal, comprising
   obtaining milk from a transgenic mammal selected from the group consisting of sheep, mice, pigs, cows, rabbits and goats having introduced into its germline a nucleic acid construct comprising:
   (a) a mammary epithelial specific promoter sequence,
   (b) a milk protein specific signal sequence,
   (c) a sequence other than a signal sequence which encodes a sufficient portion of the amino terminal coding region from the amino terminal end of a milk protein to allow secretion in the milk of a transgenic mammal of a non-secreted protein; and
   (d) a sequence encoding a non-secreted protein,
   wherein elements (a), (b), (c), and (d) are operatively linked in the order recited and the heterologous non-secreted protein is expressed and secreted into the milk of the mammal, thereby providing a non-secreted protein in the milk of the mammal.

10. The method of claim 9, wherein the non-secreted protein is inactive.

11. The method of claim 9, wherein the mammary epithelial specific promoter is selected from the group consisting of a beta lactoglobulin promoter, whey acid protein promoter, β-casein promoter and a lactalbumin promoter.

12. The method of claim 9, wherein the milk protein specific signal sequence is β-casein signal sequence.

13. The method of claim 9, wherein the sequence encoding the non-secreted protein is of a human origin.

14. The method of claim 9, wherein the sequence encoding the non-secreted protein codes for a truncated, nuclear, or a cytoplasmic polypeptide.

15. The method of claim 9, wherein the sequence encoding the non-secreted protein codes for glutamic acid decarboxylase or myelin basic protein.

16. The method of claim 9, wherein the non-secreted protein-coding sequence codes for an inactive form of a glutamic acid decarboxylase.

17. The method of claim 9, wherein the non-secreted protein is purified from the milk of a transgenic mammal.

18. The method of claim 9, wherein the non-secreted protein codes for an inactive form of myelin basic protein.

19. The method of claim 9, wherein the amino terminal coding region is from a milk protein selected from the group consisting of caseins, beta lactoglobulin, whey acid protein, and lactalbumin.

20. An isolated nucleic acid construct which comprises:
(a) a mammary epithelial specific promoter;
(b) a milk protein specific signal sequence which can direct the secretion of a protein;
(c) a sequence other than a signal sequence which encodes a sufficient portion of the amino terminal coding region from the amino terminal end of a milk protein to allow secretion in the milk of a transgenic mammal of a non-secreted protein; and
(d) a sequence which encodes a non-secreted protein, wherein elements (a), (b), (c), and (d) are operatively linked in the order recited.

21. The construct of claim 20, wherein the mammary epithelial specific promoter sequence is the β-casein promoter sequence.

22. The construct of claim 20, wherein the milk protein specific signal sequence is the β-casein signal sequence.

23. The construct of claim 20, wherein the sequence encoding the non-secreted protein is of a human origin.

24. The construct of claim 20, wherein the sequence encoding the non-secreted protein codes for a truncated, nuclear, or a cytoplasmic polypeptide.

25. The construct of claim 20, wherein the sequence encoding the non-secreted protein codes for glutamic acid decarboxylase or myelin basic protein.

26. The construct of claim 20, wherein the milk protein is β-casein.

27. The construct of claim 20, wherein the amino terminal coding region comprises about 10% to 30% of the amino terminal coding region of a milk protein.

28. A method of making and secreting a non-secreted protein comprising:
introducing into a mammal selected from the group consisting of sheep, mice, pigs, cows, rabbits and goats a nucleic acid construct which comprises:
(a) a mammary epithelial specific promoter;
(b) a milk protein specific signal sequence which can direct the secretion of a protein;
(c) a sequence other than a signal sequence which encodes about 10% of the amino terminal coding region from the amino terminal end of a milk protein to allow secretion in the milk of a transgenic mammal of a non-secreted protein; and
(d) a sequence which encodes a non-secreted protein, wherein elements (a), (b), (c), and (d) are operatively linked in the order recited; and
expressing the protein, thereby producing the non-secreted protein in the milk of the transgenic mammal.

29. The method of claim 28, wherein the amino terminal coding region comprises about 20% of the amino terminal coding region of a milk protein.

30. The method of claim 28, wherein the amino terminal coding region comprises about 30% of the amino terminal coding region of a milk protein.

31. A method for providing a non-secreted protein in the milk of a transgenic mammal, comprising
obtaining milk from a transgenic mammal selected from the group consisting of sheep, mice, pigs, cows, rabbits and goats having introduced into its germline a nucleic acid construct comprising:
(a) a mammary epithelial specific promoter sequence,
(b) a milk protein specific signal sequence,
(c) a sequence other than a signal sequence which encodes about 10% of the amino terminal coding region from the amino terminal end of a milk protein to allow secretion in the milk of a transgenic mammal of a non-secreted protein; and
(d) a sequence encoding a non-secreted protein, wherein elements (a), (b), (c), and (d) are operatively linked in the order recited and the heterologous non-secreted protein is expressed and secreted into the milk of the mammal, thereby providing a non-secreted protein in the milk of the mammal.

32. The method of claim 31, wherein the amino terminal coding region comprises about 20% of the amino terminal coding region of a milk protein.

33. The method of claim 31, wherein the amino terminal coding region comprises about 30% of the amino terminal coding region of a milk protein.

34. An isolated nucleic acid construct which comprises:
(a) a mammary epithelial specific promoter;
(b) a milk protein specific signal sequence which can direct the secretion of a protein;
(c) a sequence other than a signal sequence which encodes about 10% of the amino terminal coding region from the amino terminal end of a milk protein to allow secretion in the milk of a transgenic mammal of a non-secreted protein; and
(d) a sequence which encodes a non-secreted protein, wherein elements (a), (b), (c), and (d) are operatively linked in the order recited.

35. The construct of claim 34, wherein the amino terminal coding region comprises about 20% of the amino terminal coding region of a milk protein.

36. The construct of claim 34, wherein the amino terminal coding region comprises about 30% of the amino terminal coding region of a milk protein.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 88 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

TCGACGAGAG CCATGAAGGT CCTCATCCTT GCCTGTCTGG TGGCTCTGCG GATTGCAAGA    60

GAGCAGGAAG AACTCAATGT AGTCGGTA                                      88

(2) INFORMATION FOR SEQ ID NO:2:

(i) SEQUENCE CHARACTERISTICS:
            (A) LENGTH: 88 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:2:

GATCTACCGA CTACATTGAG TTCTTCCTGC TCTCTTGCAA TGGCCAGAGC CACCAGACAG    60

GCAAGGATGA GGACCTTCAT GGCTCTCG                                      88

(2) INFORMATION FOR SEQ ID NO:3:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:3:

GATCGGTGGT A                                                        11

(2) INFORMATION FOR SEQ ID NO:4:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:4:

GATCTACCAC CGATGGGCC                                                19

(2) INFORMATION FOR SEQ ID NO:5:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:5:

CCATTGCAAG ATCTGCGTCA CAGAAGAGAC CCTCC                              35

(2) INFORMATION FOR SEQ ID NO:6:

(i) SEQUENCE CHARACTERISTICS:
            (A) LENGTH: 38 base pairs
            (B) TYPE: nucleic acid
            (C) STRANDEDNESS: single
            (D) TOPOLOGY: linear -continued

```
        (ii) MOLECULE TYPE: cDNA (xi) SEQUENCE DESCRIPTION: SEQ ID NO:6:

TCACCCATGG CTAGACGCTG ACTCGAGGAT CCTTGTCA                              38

(2) INFORMATION FOR SEQ ID NO:7:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:7:

TCGAGCCCAC CATGAAGGTC CTCATCCTTG CCTGTCTGGT GGCTCTGGCC ATTG            54

(2) INFORMATION FOR SEQ ID NO:8:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:8:

CATGGCAATG GCCAGAGCCA CCAGACAGGC AAGGATGAGG ACCTTCATGG TGGC            54
```